US007235066B1

(12) United States Patent
Narini et al.

(10) Patent No.: US 7,235,066 B1
(45) Date of Patent: Jun. 26, 2007

(54) FLUID CONTAINMENT DEVICE

(75) Inventors: Philip P. Narini, Oshawa (CA); Brenda Matloub, Waukesha, WI (US); Haitham Matloub, Waukesha, WI (US)

(73) Assignee: NewMedical Technology, Inc., Northbrook, IL (US)

( * ) Notice: Subject to any disclaimer, the term of this patent is extended or adjusted under 35 U.S.C. 154(b) by 29 days.

(21) Appl. No.: 10/750,477

(22) Filed: Dec. 31, 2003

Related U.S. Application Data

(60) Provisional application No. 60/437,444, filed on Jan. 2, 2003.

(51) Int. Cl.
*A61B 19/12* (2006.01)
*A61M 35/00* (2006.01)
*A61G 10/00* (2006.01)

(52) U.S. Cl. ............... 604/356; 604/290; 128/853; 600/21

(58) Field of Classification Search ........... 604/355, 604/356, 332; 600/21; 128/849, 853
See application file for complete search history.

(56) References Cited

U.S. PATENT DOCUMENTS

| 542,202 | A | * | 7/1895 | Morrison .................... 604/357 |
| 762,737 | A | * | 6/1904 | Meinecke et al. ............ 604/357 |
| 998,803 | A | * | 7/1911 | Salisbury ........................ 4/518 |
| 2,972,353 | A | * | 2/1961 | Quest ............................ 312/1 |
| 3,818,896 | A | * | 6/1974 | Deaton ......................... 600/22 |
| 3,850,172 | A | * | 11/1974 | Cazalis ......................... 600/21 |
| 4,000,749 | A | * | 1/1977 | Busco .......................... 600/21 |
| 4,091,852 | A | * | 5/1978 | Jordan et al. .................. 383/3 |
| 4,602,773 | A | * | 7/1986 | Craven, Jr. .................... 5/646 |
| 4,656,997 | A | * | 4/1987 | Morales-George .......... 128/897 |
| 4,817,651 | A | * | 4/1989 | Crisp et al. .............. 134/102.1 |
| 5,107,859 | A | * | 4/1992 | Alcorn et al. ............... 128/853 |
| 5,178,162 | A | * | 1/1993 | Bose .......................... 128/849 |
| 5,312,385 | A | * | 5/1994 | Greco ......................... 604/356 |
| 5,316,541 | A | * | 5/1994 | Fischer ........................ 600/21 |
| 5,437,602 | A | * | 8/1995 | Polyakov et al. ............. 600/21 |
| 5,447,504 | A | * | 9/1995 | Baker et al. ................ 604/289 |
| 5,609,163 | A | * | 3/1997 | Beard ......................... 128/846 |
| 5,743,435 | A | * | 4/1998 | Tomic ......................... 222/105 |
| 5,970,979 | A | * | 10/1999 | Christofel et al. .......... 128/849 |
| 6,083,209 | A | * | 7/2000 | Marasco, Jr. ............... 604/290 |
| 6,210,381 | B1 | * | 4/2001 | Morse ........................ 604/289 |
| 6,217,507 | B1 | * | 4/2001 | Bonvik ........................ 600/21 |
| 6,314,958 | B1 | * | 11/2001 | Harroll et al. .............. 128/849 |
| 6,461,290 | B1 | * | 10/2002 | Reichman et al. ............ 600/21 |
| 6,793,617 | B2 | * | 9/2004 | Ford et al. .................... 600/21 |
| 7,096,871 | B2 | * | 8/2006 | Lee et al. ................... 128/853 |
| 2002/0148857 | A1 | * | 10/2002 | Savage et al. .............. 222/107 |
| 2004/0045557 | A1 | * | 3/2004 | Lee et al. ................... 128/853 |

\* cited by examiner

*Primary Examiner*—Tatyana Zalukaeva
*Assistant Examiner*—Paula L. Craig
(74) *Attorney, Agent, or Firm*—Vedder, Price, Kaufman & Kammholz, P.C.; W. Dennis Drehkoff

(57) ABSTRACT

A wound irrigation/fluid containment system having a flexible bag body defining a containment space, the bag body including walls and at least one opening with a seal, means for accessing through the bag body walls to the containment space and means for inflating portions of the walls to provide rigidity and strength to the walls. The containment device isolates a wound on a person and is capable of draining fluids away from the wound.

3 Claims, 7 Drawing Sheets

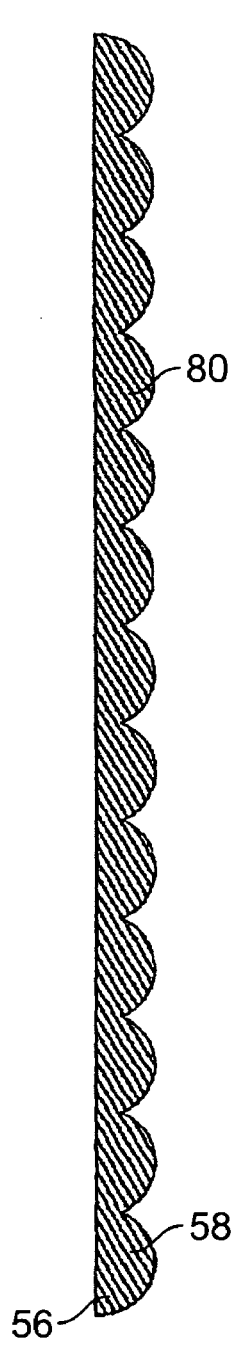
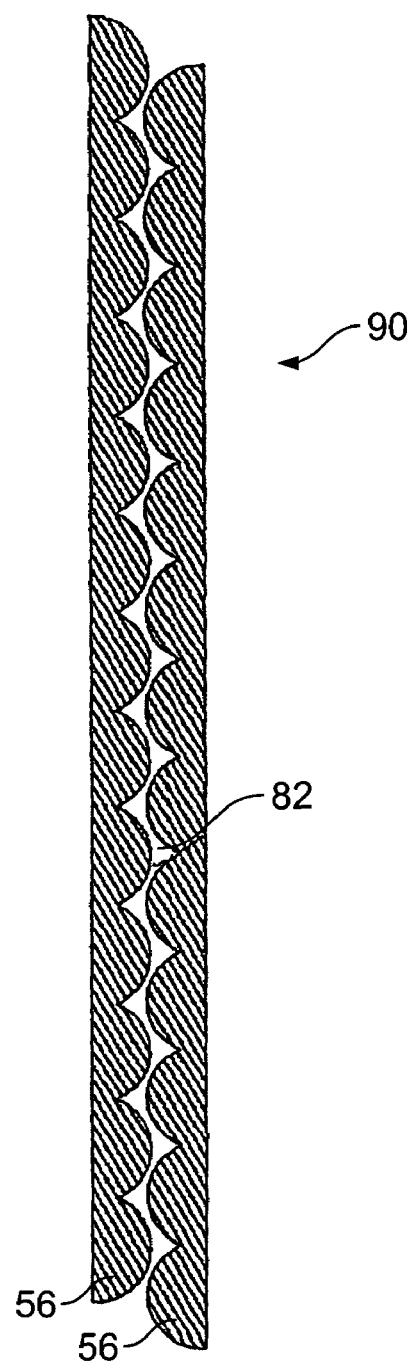
FIG. 7  FIG. 8

FLUID CONTAINMENT DEVICE

This application claims the benefit of priority to U.S. Provisional Application No. 60/437,444 filed Jan. 2, 2003.

FIELD OF THE INVENTION

The invention relates generally to surgical devices and more particularly to a wound irrigation/fluid containment system (WICS) that isolates a wound on a person upon which wound treatment is to be performed.

BACKGROUND OF THE INVENTION

Standard treatment for all wounds requires cleansing or washing to remove foreign material and to decrease bacterial contamination. Safety considerations require isolation of the wound-care-provider (first responder, nurse, physician, surgeon, assistants) from body fluids and any contaminated irrigation fluid.

Debridement is the removal of foreign matter such as dirt, glass or dead tissue, whereas irrigation is the flushing of fluid over the wound to remove smaller particles and bacteria to decrease the possibility of infection. A collection pan or receptacle is placed under the wound that is to be treated in order to collect the irrigation fluid used during the irrigation and debridement process.

It is not uncommon that during irrigation and debridement procedures that fluid can plash onto the wound-care-provider, equipment and surroundings. In other words, the collection pan placed under the wound usually will not catch all of the irrigation or wound fluids that are present during the irrigation and debridement procedure. This is of particular concern should the patient have blood-borne infection such as HIV, Hepatitis or Cytomegalovirus, thereby putting the wound-care-provider at risk of contracting an infectious disease. There are times when a patient may not be aware that they have contracted an infectious disease and hence the adoption of universal precautions has been recommended.

Therefore, there is a need for a fluid containment system that provides a barrier to the wound-care-provider to splash of contaminated irrigation fluids or body fluids. This system must contain body and irrigation fluids, as completely as possible, collect, enclosed and allow safe and complete drainage of said fluids, but yet allow freedom of movement of the wound-care-provider to be able to attend to the patients needs without undue restrictions.

DESCRIPTION OF THE PRIOR ART

U.S. Pat. No. 5,178,162 titled Splash and Spill Resistant Extremity Irrigation and Debridement Fluid containment device granted Jan. 12, 1993, filed by inventor William Jo. Bose on Apr. 14, 1992 describes a fluid containment device which attempts to isolate an extremity of the body and provide for a drainage means for fluids used during irrigation and to allow access by the surgeon to perform various functions. The fluid containment device depicted and described in U.S. Pat. No. 5,178,162 contemplates the use of fenestrations or access ports for the surgeon, including apertures for nozzles and as well a resealable slit or opening for access to the affected extremity during surgery. In addition, there is a drainage plug which is used for the removal of irrigation fluids as they are applied to the patient.

In practise this fluid containment device is impracticable because it tends to collapse particularly when any vacuum is applied to the drainage plug to remove the irrigation fluids. In order to prevent collapsing of this fluid containment device, the amount of suction applied to the drainage plug is minimized or avoided completely until after the surgery is complete, at which time a vacuum can be applied and the fluid removed. With this drape all fluids can not be removed because of pockets of fluid which become isolated from the vacuum source.

The present invention address these issues and provides for a bag which maintains some rigidity or shape and provides resistance to collapsing of the fluid containment device or drape itself and also provides for a more complete evacuation of irrigation fluids that may become trapped in between the membrane walls of the fluid containment device by use of special surface textures of the membrane itself

SUMMARY OF THE INVENTION

The present invention a fluid containment device comprises:

A fluid containment device comprising:

a) a flexible bag body defining a containment space;

b) said bag body including walls and at least one opening, said opening including a means for sealing off said end;

c) a means for accessing through said bag body walls and into said containment space; and d) a means for inflating portions of said walls to provide rigidity and strength to said walls.

Preferably further including a means for draining fluids captured within said containment space.

Preferably wherein said bag body comprised of at least two flexible membranes.

Preferably wherein said bag body including an inner membrane and an outer membrane disposed adjacent each other to form a double layered wall.

Preferably wherein said inflating portions defined by the space between said inner and outer membranes.

Preferably wherein said inflating portions comprising inflatable chambers extending between sealed locations where said outer and inner membranes are sealed together.

Preferably wherein said inflatable chambers including horizontal inflatable chambers and vertical inflatable chambers.

Preferably wherein said inflatable chambers being tubular in shape.

Preferably wherein said membranes including an inner dimpled surface such that when said bag body collapses onto itself voids are formed between said bag walls forming drainage pathways for any entrapped fluids in said fluid containment device.

Preferably wherein said sealing means including Velcro® male and female connectors for sealing off said collar around or against a body part.

Preferably wherein said sealing means including adhesive means for sealing off said collar around or against a body part.

BRIEF DESCRIPTION OF THE DRAWINGS

The invention will now be described by way of example only with reference to the following drawings as follows:

FIG. 7 is an enlarged cross-sectional view of the inner membrane showing a dimpled surface structure.

FIG. 8 is a schematic enlarged cross-sectional view of two inner membranes contacting each other showing the membranes in the collapsed position.

DETAILED DESCRIPTION OF THE PREFERRED EMBODIMENT

Figure 1:
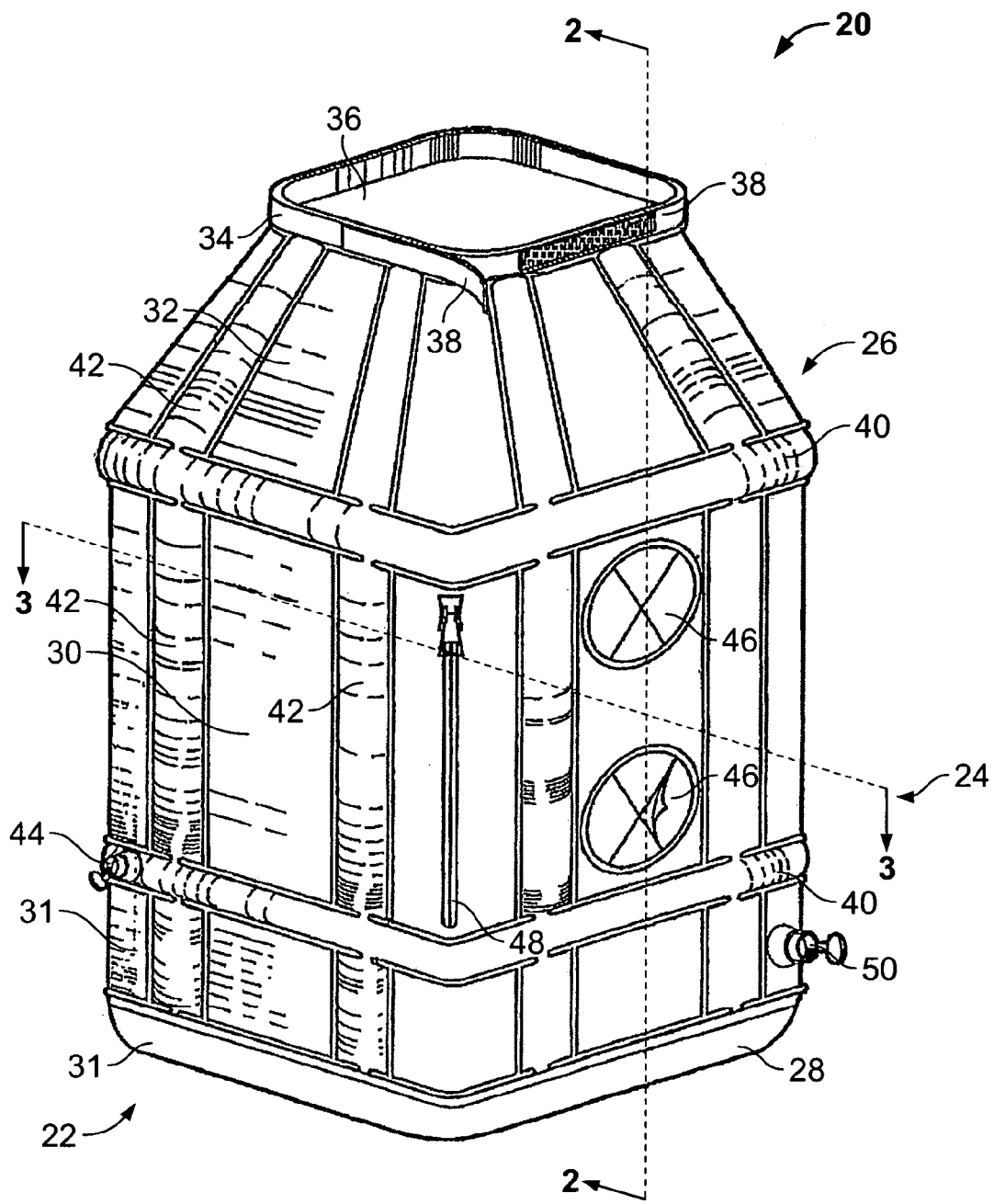
FIG. 1 is a schematic perspective upright frontal view of the wound irrigation/fluid containment system.

Referring now to FIGS. 1 through 6 in particular, the present invention a fluid containment device shown generally as 20 includes the following major components, namely bag body 22 having a lower section 24 and an upper tapered section 26. Fluid containment device 20 includes bottom 28, walls 31 including side walls 30 and tapered walls 32, culminating and attached to a collar 34 defining an opening 36 which can be adjusted with velcro fastener 38.

The shape of fluid containment device 20 is maintained with horizontal inflatable chambers 40 which are interconnected with vertical inflatable chambers 42, wherein air can be injected into vertical inflatable chambers 42 as well as horizontal inflatable chambers 40 through air inlet/outlet 44. Fluid containment device 20 defines a containment space 21 which can receive and house various appendages for subsequent surgical procedures.

Optionally fluid containment device 20 includes access ports 46 as well as sealable openings 48 and also is fitted with a drain plug 50 for draining of any liquids which find their way into fluid containment device 20.

Figure 3:
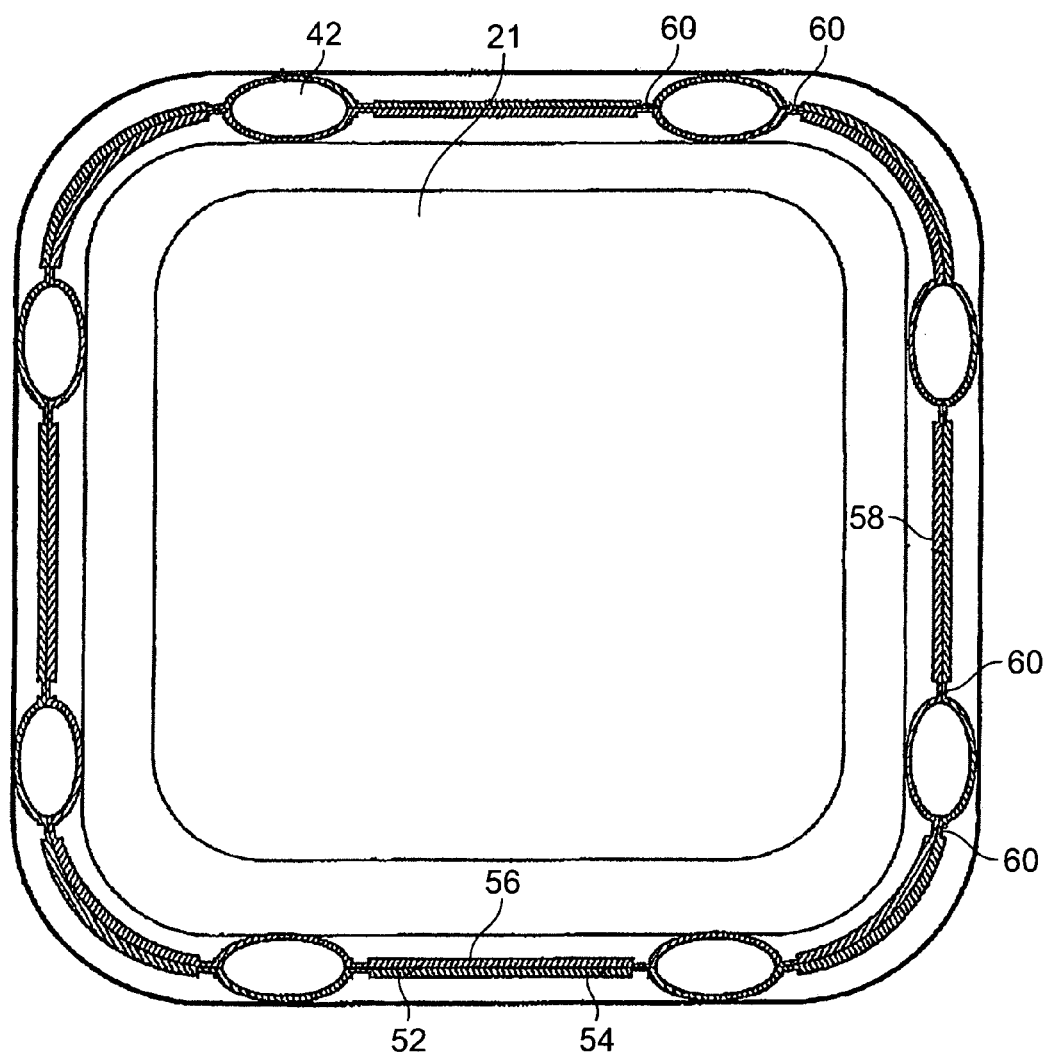
FIG. 3 is a schematic cross-sectional view taken along lines 3—3 of FIG. 1.

Referring now specifically to FIG. 3 which shows the construction of side walls 30, it is apparent that side walls 30 are comprised of double layered walls 52 which include an outer membrane 54 and an inner membrane 56. Two membranes namely, inner and outer membranes 56 and 54 respectively, defines vertical inflatable chamber 42. For example as shown in FIG. 3 vertical inflatable chamber 42 is defined by the space between sealed locations 60. In order to prevent escape of air or other gases from either vertical inflatable chambers 42 or horizontal inflatable chambers 40, the outer and inner membranes 54 and 56 are sealed off at seal location 60 on either side of vertical inflatable chambers 42.

Figure 2:
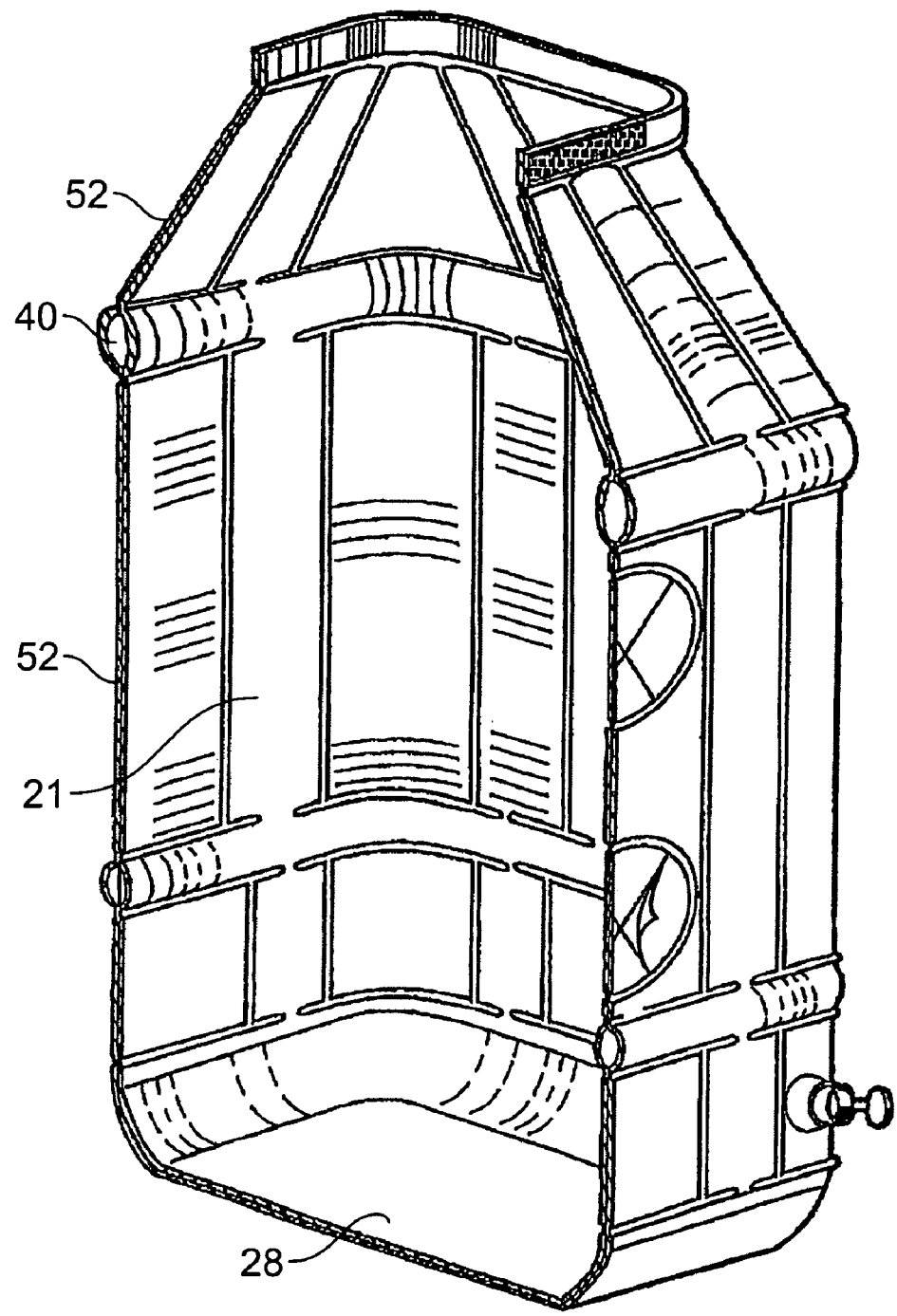
FIG. 2 is a schematic partial cut away view of the fluid containment device taken along lines 2—2 of FIG. 1.

Referring now to FIG. 2, the same structure is used to define both the tapered walls 32, the bottom 28 as well as side walls 30. Horizontal inflatable chambers 40 are defined in an analogous manner as vertical inflatable chambers 42, namely by using an inner and outer membrane 56 and 54 which is sealed off at sealed locations 60 on either side of horizontal inflatable chambers 40. In other locations other than the sealed locations, the inner and outer membranes 56 and 54 essentially lie adjacent each other to form a double layered wall 52 which defines the bottom 28, side walls 30 and tapered walls 32.

In Use

Figure 4:
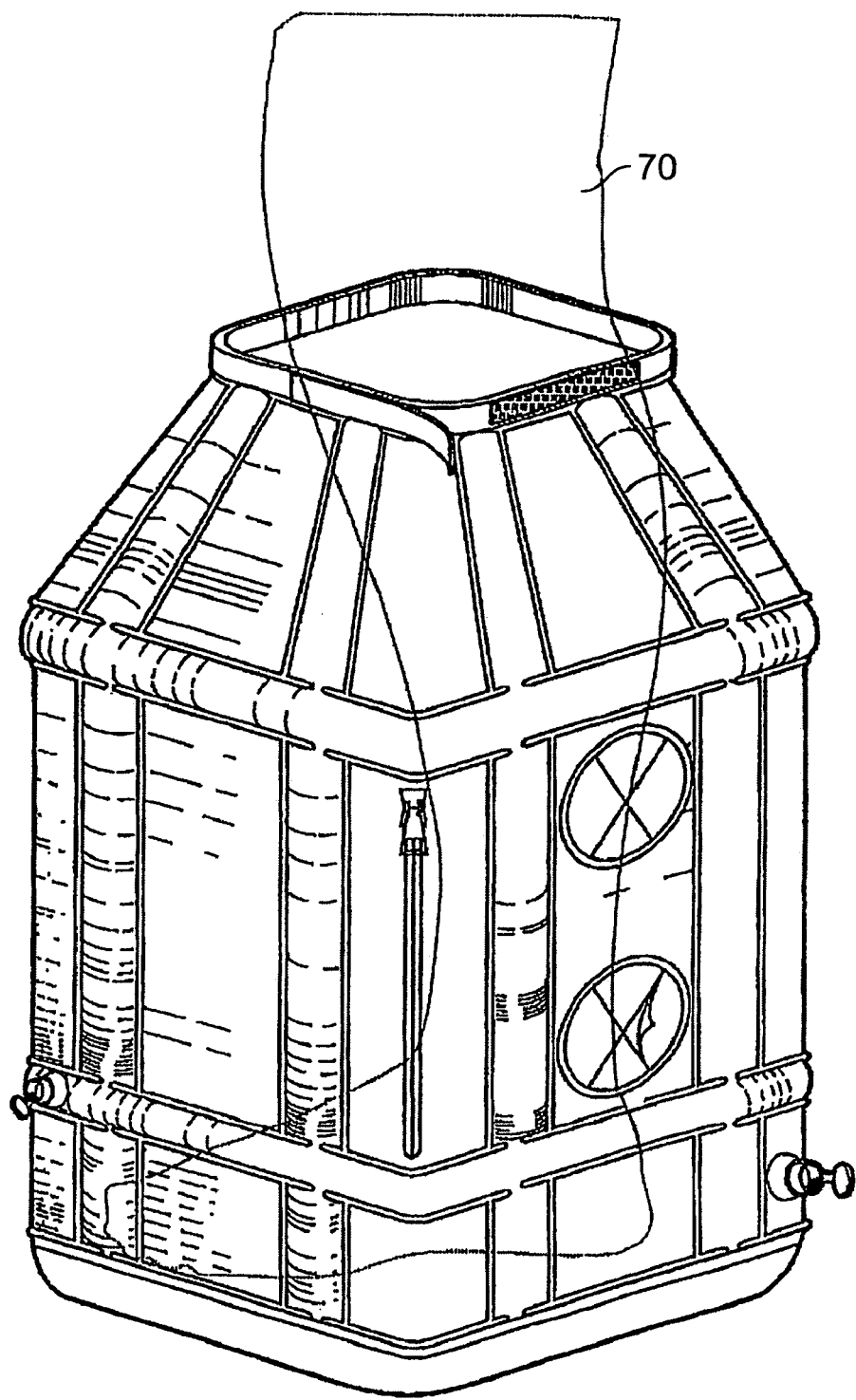
FIG. 4 is a schematic perspective upright view of the fluid containment device shown in FIG. 1 together with placement of as a leg therein.
Figure 5:
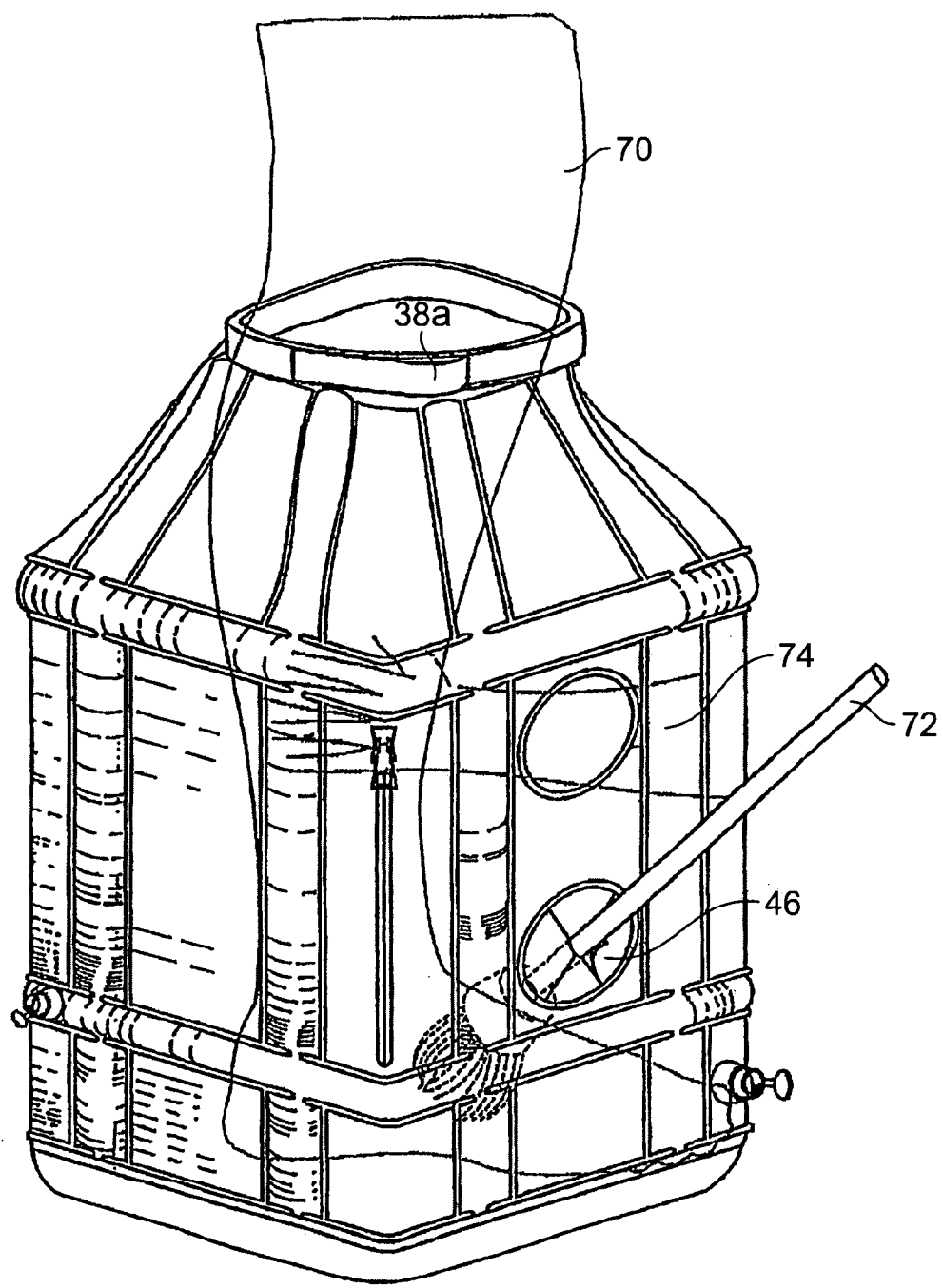
FIG. 5 is a schematic perspective upright view of the fluid containment device shown in FIG. 1 together with placement of an extremity such as a leg therein and in addition showing an instrument and a hand being placed through the access ports.

Referring now to FIGS. 4 and 5 in particular, in order to use fluid containment device 20, first of all air is injected into air inlet 44 in order to inflate horizontal inflatable chambers 40 as well as vertical inflatable chambers 42 in order to give rigidity and shape to fluid containment device 20. Horizontal inflatable chambers 40 and vertical inflatable chambers 42 are all interconnected in the embodiment shown in the attached drawings so that only one air inlet 44 is required to inflate all of the vertical inflatable chambers 42 and horizontal inflatable chambers 40. In practise it is possible to isolate some or all of the vertical inflatable chambers and horizontal inflatable chambers by supplying them with individual air inlet and outlets as is practical. The horizontal inflatable chambers 40 and vertical inflatable chambers 42 are tube like in structure. Supplying sufficient air pressure within the inflatable chambers provides rigidity to the fluid containment device giving it a certain structure and shape, thereby preventing collapse of fluid containment device 20 during its use in operations.

Once fluid containment device 20 is inflated by injecting air through inlet/outlet 44 and into the inflatable chambers, one can then place the extremity of a body as for example a leg 70 as shown in FIG. 4 into the opening 36 defined by collar 34 of fluid containment device 20. The hook and loop fasteners 38 can be used to then seal off the upper portion of the extremity or leg 70 as shown in FIG. 4 such that fluid is prevented from leaking past and out the top of fluid containment device 20.

It is possible to have other sealing arrangements for collar 34. For example adhesive tape 38a may be used to augment or replace hook and loop fasteners, as shown in FIG. 5. The collar may be so designed so as to seal off against a flat portion of the body such as a torso or chest with little or no portion of the body entering into containment space 21. The collar may also be made of rubber or flexible material for sealing off opening 36 or may have some type of draw string mechanism. Persons skilled in the art will recognize that opening 36 may sealed off in many different manners that are known in the art with some examples described above.

It is also possible to have two openings namely one at each end of the bag. This variation is not shown in the drawings but would be useful for placing an arm through the bag to work on an upper portion of an arm for example. In this case the bag would be sealed off at an upper portion of the arm and at a lower portion of the arm.

Referring now to FIG. 5, one can see that various instruments 72 or a hand 74 can be placed through access ports 46 or even through sealable opening 48 in order to work on the injured extremity or leg 70 as shown in FIG. 5.

Referring now to FIGS. 1 and 5, 46 represents a sealable access port that allows approach by hand 74 but will otherwise remain sealed, preventing exit of fluids. Also, upon withdrawal of hand 74, port 46 can again become sealed, again, minimizing risk of fluid leakage.

In use a vacuum can be applied to drain plug 50 such that during debridement and/or irrigation operations, any liquid that enters fluid containment device 20 can be collected in the bottom 28 of fluid containment device 20 and once the liquid reaches drain plug 50 it can be drained out or evacuated from fluid containment device 20. The inflatable chambers 40 and 42 resist, collapse of fluid containment device 20 thereby allowing one to continuously drain fluid from fluid containment device 20 during its use in an operation.

Figure 6:
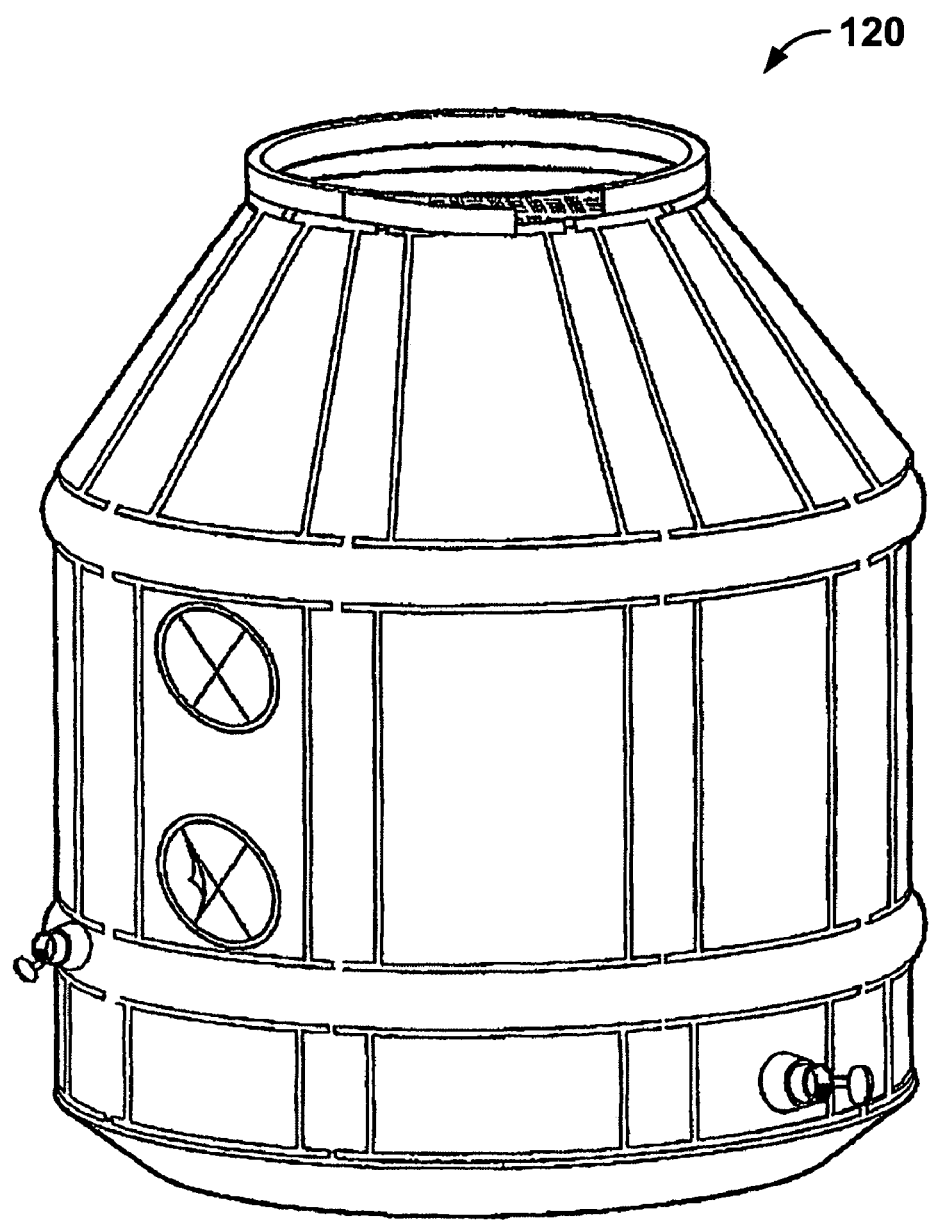
FIG. 6 is a schematic perspective upright view of an alternate geometry of the fluid containment device wherein the bag takes on a rounded shape verses the square shape as shown in FIG. 1.

FIG. 6 depicts a fluid containment device 120 that is not necessarily square or rectangular in shape as shown in FIGS.

1 through 5, but can take on other shapes including rounded as shown in FIG. 6 and any other shape that is practically usable including an elongated bag having various lengths and widths to be able to accommodate various extremities of different shapes. The features and mode of operation of surgical bag 120 are analogous to surgical bag 20.

Referring now to FIGS. 7 and 8, FIG. 7 depicts a magnified cross-sectional view of inner membrane 56 showing the inner surface 58 having a dimpled or ridged surface 80. FIG. 8 shows two inner membranes 56 which have impinged upon each other in a collapsed position 90 showing two dimpled surfaces 80 contacting each other. This will occur for example should a fluid containment device 20 collapse under the suction which is applied to drain plug 50 being so great that it collapses fluid containment device 20 thereby two inner membranes 56 come in contact with each other upon collapse. Two dimpled surfaces 80 contact each other and thereby form voids 82 between the dimples of dimpled surface 80 such that any vacuum applied to drain plug 50 would still be able to extract any liquid found between the two inner membranes 56 and collapsed position 90.

In other words dimpled surface 80 ensures that even if two inner membranes 56 collapse one onto each other as shown in FIG. 8, there always remains some voids 82 as shown in FIG. 8 in collapsed position 90, such that liquid can be extracted.

It should be apparent to persons skilled in the arts that various modifications and adaptation of this structure described above are possible without departure from the spirit of the invention the scope of which defined in the appended claim.

What is claimed is:

1. A fluid containment device comprising:
   a) a flexible bag body defining a containment space;
   b) said bag body including walls having at least two flexible membranes including an inner membrane and an outer membrane disposed adjacent to each other forming a double layered wall and at least one opening, said opening dimensioned and configured for receiving a body part or limb through said bag body and into said containment space, said opening including a means for sealing off the opening around the body part or limb;
   c) means for accessing through said bag body walls and into said containment space, said means for accessing being separate from the opening;
   and
   d) means for inflating portions of said walls defined by the space between said inner and outer membranes comprising tubular inflatable chambers extending between sealed locations where said outer and inner membranes are sealed together to provide rigidity and strength to said walls and prevent collapse of the fluid containment device when the tubular inflatable chambers are inflated;
   further including a means for draining fluids captured within said containment space;
   wherein said inner membrane of said bag walls includes an inner surface, said inner surface facing said containment space; and
   said inner surface including a plurality of dimples, said dimples being integral with said inner membrane and protruding into said containment space, said dimples being dimensioned and configured such that when said tubular inflatable chambers are deflated and said bag body is collapsed onto itself voids are formed between said bag walls, said voids forming drainage pathways for any entrapped fluids in said containment space.

2. The fluid containment device claimed in claim 1 wherein said sealing means includes hook and loop male and female connectors for sealing off the opening around the body part or limb.

3. The fluid containment device claimed in claim 1 wherein said sealing means includes adhesive means for sealing off the opening around the body part or limb.

* * * * *